US00PP10975P

United States Patent [19]

Roberson

[11] Patent Number: Plant 10,975

[45] Date of Patent: Jun. 22, 1999

[54] HEMEROCALLIS PLANT NAMED 'ROBBOBMAR'

[76] Inventor: Robert J. Roberson, 31706 E. Pink Hill Rd., Grain Valley, Jackson County, Mo. 64029

[21] Appl. No.: 08/987,484

[22] Filed: Dec. 9, 1997

[51] Int. Cl.[6] ..... A01H 5/00

[52] U.S. Cl. ..... Plt./312

[58] Field of Search ..... Plt./87.4, 312

*Primary Examiner*—Howard J. Locker
*Assistant Examiner*—Ashwin Mehta
*Attorney, Agent, or Firm*—Rothwell, Figg, Ernst & Kurz

[57] ABSTRACT

The new and distinct daylily plant substantially as herein shown and described, particularly characterized by its ability to produce multiple repeat bloom scapes, maintain a consistently dwarf growth habit, multiply rapidly, establish and bloom promptly, produce well formed single, then double, yellow-gold blooms which have slight fragrance and performs well across multiple USDA zones.

2 Drawing Sheets

SUMMARY OF THE INVENTION

This invention relates to a new and distinct daylily distinguished by it's consistent, very dwarf growth habit, dependably near-continuous blooming habit, unique bloom form and presentation (single floret in initial cycle and double floret in subsequent cycles), rapid growth and fan increase, tendency to establish quickly and begin blooming promptly after planting, slight bloom fragrance and the slow tendency to set seed.

BACKGROUND OF THE INVENTION

This new variety of daylily plant originated as a seedling selected from a group of seedlings planted by me at my ranch in Grain Valley, Mo., and resulting from my crossing of the clonal cultivar 'Stella de Oro' (not patented) with the variety 'Puddin' (not patented). My objecting was to produce a plant having near continuous blooming habit, dwarf growth habit and rapid multiplication rate. A further objective was to produce such a plant that would have a tendency to establish quickly and begin blooming promptly, be slow to set seed and have unique double bloom form and fragrance.

This new plant was selected for propagation because it most closely possessed the advantageous features that I sought and asexual reproduction of the selected plant was observed by natural division at Grain Valley, Mo.

During the course of propagation of this new plant on a more-or-less commercial scale at my daylily ranch in Grain Valley, Mo., I have observed that the new plant is very hardy when grown in zone 4–9 and is particularly capable of near continuous blooming throughout the perennial flowering season, maintaining a consistently dwarf growth habit and multiplies rapidly. Furthermore, I have observed that the new plant has a strong tendency to establish quickly and begin blooming soon after planting, has slight bloom fragrance, has attractive "double" blooms when repeat blooming, and has a very slow tendency to set seed. I have chosen to identify this new cultivar as Hemerocallis 'Robbobmar'. This cultivar is being marketed in the United States under the name MISS MARY MARY™.

BRIEF DESCRIPTION OF THE DRAWING

The accompanying photograph shows as nearly true as it is reasonably possible to make the same, in a color illustration of this character, shows a face view of three of the flowers as they appear in "double" form from mid thru late season.

In the photograph.

DETAILED DESCRIPTION

Figure 1:
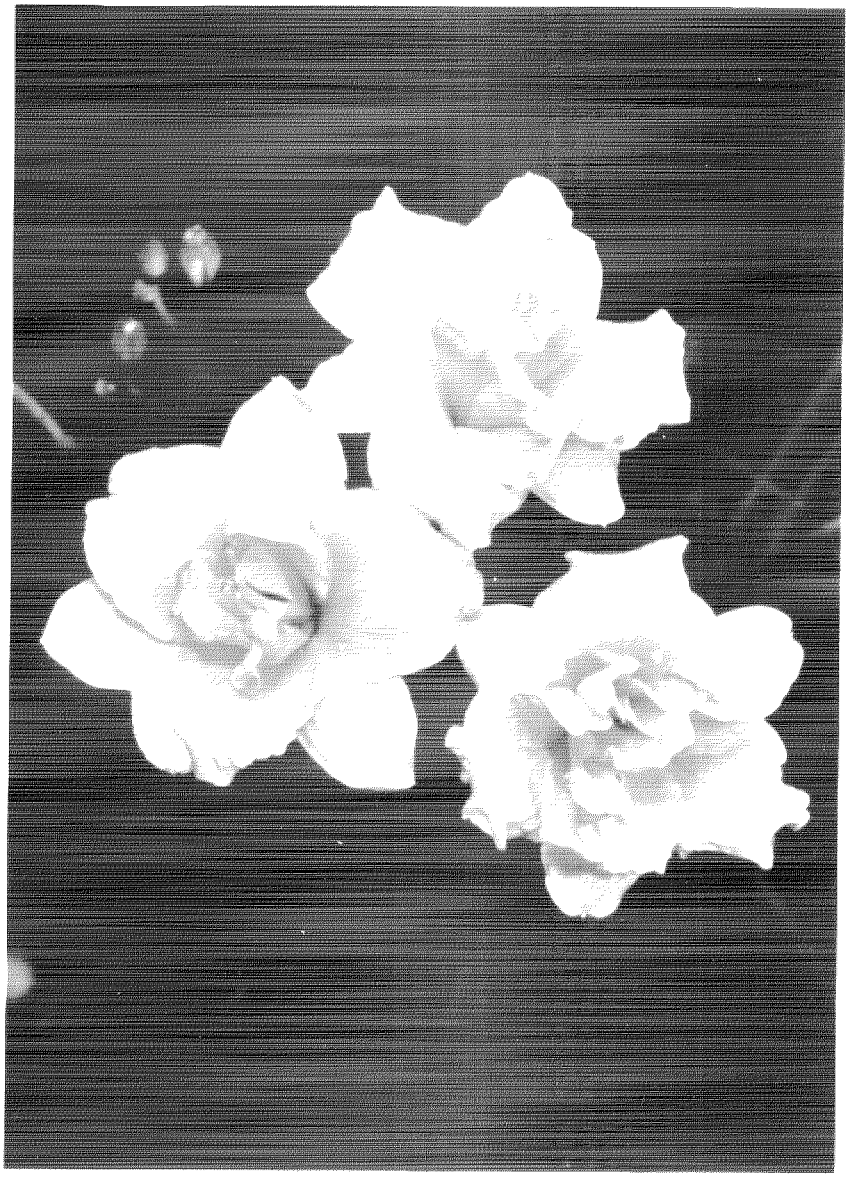
FIG. 1 illustrates the mature double flower
Figure 2:
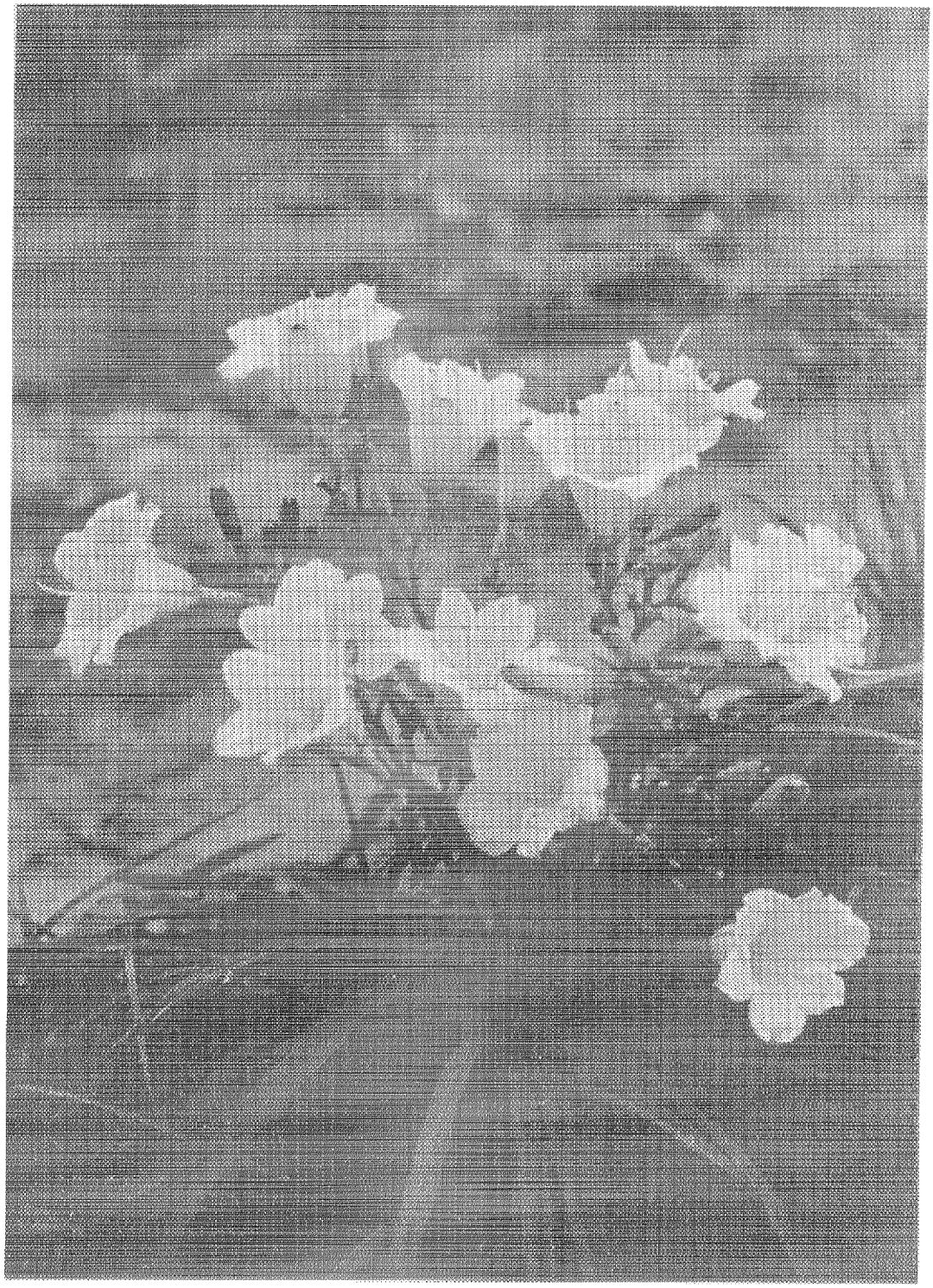
FIG. 2 illustrates the overall plant habit.

The following is a detailed description of my hybrid daylily cultivar based upon observation of plants grown at Grain Valley, Mo. during 1989–1994. All colors being noted as compared with the Pantone Matching System (PMS). The measurements and colors were recorded from mature plants grown in the vicinity of Grain Valley, Mo., unless stated otherwise.

The Plant

Origin: It should be noted that the plant was initially selected from a daylily planting being grown near Grain Valley, Mo. in a cultivated area and has since been reproduced by natural vegetative division in the vicinity of Grain Valley, Mo. with the new and distinct characteristics stated herein, found to be maintained through successive generations as before recited.

Parentage:
- *Seed parent.*—'Stella de Oro' (not patented).
- *Pollen parent.*—'Pudden' (not patented).

Classification:
- *Botanic.*—Hemerocallis hybrid.
- *Commercial.*—Daylily cultivar 'Robbobmar'.

Form: Single stem, erect and stately scape from a fan shaped plant made up of narrow arching grass-like, long keeled glabrous leaves 2-ranked at the base of the scape.

Foliage:
- *Quantity.*—Abundant, a mature plant having about 12 leaves.
- *Leaf size.*—About 0.8" wide and about 10" long.
- *Leaf shape.*—Linear and long keeled with entire margins.
- *Texture.*—Glabrous.
- *Color.*—Dark Green (PMS #349).

Scape:
- *Color.*—Medium Green (PMS #357).
- *Height.*—About 16".

The Bud

Form: Modified oblanceolate.

Size (day before opening):
- *Length.*—About 3.9 cm.
- *Width.*—About 1.1 cm.

Opening rate: About 6 hours.

Color:

*When sepals first divide.*—Yellow-green (PMS #396).

Peduncle:

*Character.*—Rigid and sturdy.

*Color.*—Dard Green (PMS #364).

The Flower

Blooming habit: Flowers begin to appear on the established plant in early season, and then repeat 2–4 more cycles, or an average of 145 days depending on USDA zone.

Flower size:

*Diameter.*—About 2⅞".

*Depth.*—About 1".

Shape: Wide, round, ruffled, overlapping, and double on repeat cycles.

Borne: Singly on the branchlets of a sturdy, erect rachis which is ramulus; each scape has at least four or five peduncles which divides into twelve or fifteen pedicels.

Average number of blooms per scape: 12.

Tepalage: The flower consists of six perianth segments (i.e., tepals) consisting of three outer tepals and three inner tepals all in an imbricated arrangement. When double blooms appear the tepals consist of 10–14 segments.

The Outer Tepals

Shape: Oblanceolate with slightly undulated entire margins and an acuminate apex.

Size: About 1⅞" long and ⅝" wide.

Texture: Slightly ribbed.

Color: Soft yellow-gold (PMS #134).

The Inner Tepals

Shape: Broadly obovate with entire undulated margins and a broadly cuspidate apex.

Color: Soft yellow-gold (PMS #134).

Texture: Slightly creped.

Size: About 1⅞" wide; 1⅝" long.

Effect of weather: Very resistant to sun and rain; substance and color holds well.

Fragrance: Slight.

Disease resistance: This cultivar, as most hemerocallis, has not been noted to be very susceptible to plant disease.

Lasting quality: Excellent.

The Reproductive Organs

Stamens:

*Number.*—Six to eight.

*Arrangement.*—Inserted individually at the summit of the perianth tube.

*Anthers.*—Arrangement: Introse; Size: 4 mm; Color: Brown (PMS #438).

*Filaments.*—Slender and 3 cm in length; Color: Pale Gold (PMS #127).

*Pollen.*—Color—Gold (PMS #123).

Pistils:

*Number.*—One.

*Style.*—Length—5 cm; Color—Pale Gold (PMS #127).

*Stigma.*—Color: White & glistening.

*Character of ovaries.*—Three celled.

*Shape.*—Oblong, becoming a loculieidally 3-valved capsule.

The Fruit (Seed Pod)

Shape: The seed pod is an ovoid capsule.

Color: Ranges from pale green (PMS #372) to olive brown (PMS #140) at maturity.

Fertility: Yes, it is fertile.

GENERAL OBSERVATIONS

'Robbobmar', with it's excellent repeat blooming habit, its unique single to double bloom form, slow tendency to set seed, dwarf growth habit, rapid growth rate and tendency to bloom soon after planting is an improved hemerocallis cultivar in the yellow gold category, and should help meet the need for good landscape performing daylilies. The market demand today for daylilies is extremely high with purchasers becoming very discriminating and requesting improved beauty and performance such as found in 'Robbobmar'. Especially in demand are dwarf repeating blooming daylilies to meet the current interest in patio and border plants that offer long term summer color.

COMPARISON TO KNOWN VARIETIES

'Robbobmar' may be compared with known varieties along the following lines: 'Stella de Oro' which is not patented is an appropriate choice for a comparison to 'Robbobmar' because of (1) the color category of yellow-gold; (2) the repeat blooming habit; and (3) the dwarf growth habit. They are very similar in these three characteristics, however, 'Robbobmar' is an improved and novel cultivar due to the consistent production of double blooms in mid to late summer.

I claim:

1. The new and distinct daylily plant substantially as herein shown and described, particularly characterized by its ability to produce multiple repeat bloom scapes, maintain a consistently dwarf growth habit, multiply rapidly, establish and bloom promptly, produce well formed single, then double, yellow-gold blooms which have slight fragrance and perform well across multiple USDA zones.

* * * * *